United States Patent [19]

Ladanyi

[11] 4,145,412
[45] Mar. 20, 1979

[54] COMPOSITION FOR APPLICATION TO ORAL CAVITY AND METHOD FOR PREPARATION THEREOF

[75] Inventor: Peter A. Ladanyi, Fort Collins, Colo.

[73] Assignee: Vipont Chemical Company, Fort Collins, Colo.

[21] Appl. No.: 768,278

[22] Filed: Feb. 14, 1977

[51] Int. Cl.$^2$ ............................................... A61K 7/26
[52] U.S. Cl. ...................................................... 424/58
[58] Field of Search .................................. 424/49–58, 424/145, 195

[56] References Cited

U.S. PATENT DOCUMENTS

| 61,802 | 2/1867 | Brown | 424/195 X |
|---|---|---|---|
| 80,101 | 7/1868 | Wallis | 424/195 X |
| 85,166 | 12/1868 | Colburn | 424/58 X |
| 107,877 | 10/1870 | Cloud | 424/195 X |
| 111,821 | 2/1871 | Danforth | 424/58 |
| 120,802 | 11/1871 | Washburn | 424/195 |
| 121,989 | 12/1871 | Brown | 424/195 |
| 123,666 | 2/1872 | Bell | 424/195 X |
| 147,858 | 2/1874 | Moye | 424/195 |
| 152,098 | 6/1874 | Forster | 424/58 |
| 211,477 | 1/1879 | Sailvail | 424/195 |
| 375,173 | 12/1887 | Marx | 424/195 |
| 396,192 | 1/1889 | Clark | 424/58 |
| 1,411,577 | 4/1922 | Mullins et al. | 424/195 X |
| 1,435,498 | 11/1922 | Resnik | 424/53 |
| 1,488,097 | 3/1924 | Creger | 424/55 |
| 1,627,963 | 5/1927 | Fuller | 424/195 |
| 1,642,653 | 9/1927 | Goldstein | 424/360 X |
| 4,022,880 | 5/1977 | Vinson et al. | 424/49 |

FOREIGN PATENT DOCUMENTS 1290627   9/1972   United Kingdom.

OTHER PUBLICATIONS

Hocking, A Dictionary of Terms in Pharmacognosy, Chas. C. Thomas, Springfield, Ill. (1959) pp. 199–200 "*Sanguinaria canadensis*".

Steinmetz, Codex Vegetabilis (1957) Amsterdam, Neth. #1018, "*Sanguinaria canadensis*".

Windholz et al., Merck Index, 9th Ed. (1976) Merck & Co., Rahway, N. J. #8111, "Sanguinaria", #8112, "Sanguinarine", #2007, "Chelerythrine", #7684, "Protopine".

*Primary Examiner*—Shep K. Rose
*Attorney, Agent, or Firm*—Richard D. Law

[57] ABSTRACT

An innocuous purified extract of *Sanguinaria canadensis* is compounded at from 0.1% to 40% with a suitable paste or a liquid to be used in an oral cavity for cleaning teeth, refreshing the cavity, and conditioning the fleshy parts of the cavity.

5 Claims, No Drawings

COMPOSITION FOR APPLICATION TO ORAL CAVITY AND METHOD FOR PREPARATION THEREOF

PRIOR ART

*Sanguinaria canadensis,* Linne (family Papavaracease) is commonly known as Bloodroot, Redroot, Puccoon, Teterwort, etc, is a perennial herb native to North America. The plant and its juices have been used for various purposes during the course of pre-history as well as written history. It has been used as a natural historic folk remedy medicine. The plant has been generally used whole, either undried (fresh) or dried. The usual proceedure is to powder the dried plant and mix it with a carrier. This folk remedy has been tried for such things as asthma, bronchitis, dysentery, ringworm, and a substantial list of other ailments.

However, the rhizome of the plant has not found favor in more modern times since Sanguinaria is a local irritant, which in relatively mild doses, up to toxic quantities, produces epigastric burning with vomiting, tormenting thirst, faintness, dimness of vision, vertigo, and alarming prostration. In doses of about 1 gm it is a violent emetic. The present principle use of the Sanguinaria is as a stimulant expectorant in cough syrups.

An early patent, U.S. Pat. No. 209,331, describes the use of Bloodroot, zinc chloride and kerosene oil in equal proportions for open sores. U.S. Pat. No. 433,257 describes a salve of pulverized bloodroot, armenian bole, powdered rosin, lard and Stockholm tar in a treatment for piles. U.S. Pat. No. 2,344,830 describes the use of zinc chloride, stibnite and bloodroot to fix and outline diseased tissue for excising by surgery.

Sanguinarine, chelerythrine and other chemicals are known in Bloodroot, but recovery of these materials has involved fairly elaborate procedures including one or generally more chromatographic separation steps. Such is not feasible for commercial purposes of producing an innocuous extract from the rhizome of bloodroot.

PRESENT INVENTION

The present invention relates to oral cleansing preparations and in particular to toothpaste using a special extract of *Sanguinaria canadensis* as a portion of the preparation. The special extract in the amounts utilized does not have the disagreeable properties of the powdered rhizome, and with other ingredients provides an oral cavity and tooth cleansing agent, an excellent breath freshner and an oral cavity tissue conditioner.

The composition of the present invention, in the form of a toothpaste, provides easily available oral application. This application may be accomplished by a user. The extract of the bloodroot is compatible with the materials used in the formulation of toothpaste. The composition may be pasty in form (toothpaste) or as a powder.

The *Sanguinaria canadensis* extract is produced by treating a finely cut or ground bloodroot with an organic solvent, such as methanol. The bloodroot is thoroughly stirred with several volumes of the solvent, and is maintained in the solvent for 24 hours or more, at a temperature of about 60° C. Subsequently, the solution is filtered and the methanol evaporated. The residue is dissolved in chloroform, treated with concentrated hydrochloric acid, filtered and then dried. This dried extract is generally taken up in warm glycerin (65° C.) for mixing with a carrier.

The extract from the bloodroot may be employed in amounts by weights, of from about 0.1% to about 50%, and preferably from about 1.00% to about 10.0% of the mixture, by weight.

A toothpaste additive of the extract is prepared from the following:

|   | Amount | By Weight |
|---|---|---|
| 1. Glycerin | 758 g | 75.8% |
| 2. Water | 101 g | 10.1% |
| 3. Zinc Chloride | 136 g | 13.6% |
| 4. Bloodroot Extract (as made above) | 5 g | 0.5% |

The glycerin is weighed into a vessel and heated to about 65° C. The zinc chloride is dissolved in deionized water, and this solution is filtered and added to the bloodroot extract and stirred. This forms a lumpy paste which is placed in a mixing bowl. The remainder of the paste is washed into the vessel with the warmed glycerin. The mixture is then stirred until homogenous. The amount of zinc chloride is useful from 0.1–30% and preferably about 0.1–15% by weight.

A toothpaste is prepared from the following:

| Raw Materials | Amount | By Weight |
|---|---|---|
| 1. Vipont additive | 990 g | 19.8% |
| 2. Sorbitol (70%) | 550 g | 10.0% |
| 3. Polysorbate 80 (tween 80) | 100 g | 2.0% |
| 4. Tragacanth | 105 g | 2.1% |
| 5. Penick mint C-486 | 31.25 g | 0.625% |
| 6. Saccharin, sodium | 15 g | 0.3% |
| 7. Methylparaben | 7.5 g | 0.15% |
| 8. Propylparaben | 0.75 g | 0.015% |
| 9. Dicalcium phosphate anhyd. | 300 g | 6.0% |
| 10. Dicalcium phosphate $2H_2O$ | 1850 g | 37.0% |
| 11. Dionized water | 1100.5 g | 22.01% |

The bloodroot extract additive as prepared above, is placed in a mixing bowl and the sorbitol is added. The polysorbate 80 (tween 80) is added and the mixture is stirred. The tragacanth is added in small portions to avoid lumping and the mixture is stirred continuously during the addition. The mint flavoring is added and the mixture stirred until homogenous. At this point, the saccarin and parabens are added with continued stirring. Anhydrous dicalcium phosphate is added in small portions with stirring. The dicalcium phosphate dihydrate is then added in portions with stirring. Some portions of the water must be added along with the phosphate to maintain a good consistancy for thorough mixing. The remaining water is added, and the mixture stirred to the desired consistancy of toothpaste. A solution made from the paste is about neutral as to PH. The amount of zinc chloride is useful in an amount of 0.1–30% by weight, and in the paste from about 0.1 to 3 weight percent.

The toothpaste is used in the normal manner, one or more times a day. The toothpaste is an excellent cleaning agent, and a breath freshner. Use for some 30 days on a regular basis showed improved tissue condition of the oral cavity. The thirty day application promotes normal tissue and tends to reduce the bleeding associated with vigorous brushing. Other effects are clean teeth and a refreshed breath.

What is claimed is:

1. Composition for application to oral cavities consisting of:
   (a) an extract of Sanguinaria canadensis, produced by treating cut or ground bloodroot with methanol by maintaining the solids with the solvent for about 24 hours at about 60° C., filtering the resultant solvent and evaporating it to dryness and the resultant residue is dissolved in chloroform and adjusted to an acid pH with HCl and dried, and the resultant residue dissolved in glycerine, in an amount of from 0.1 weight percent to 40.0 weight percent, and from 0.1–30 weight percent of zinc chloride, and (b) an innocuous carrier arranged for application to an oral cavity.

2. The composition of claim 1 wherein said extract is present in amount of 1.0 weight percent to 10 weight percent.

3. The composition of claim 2 wherein said innocuous carrier is a toothpaste base.

4. The composition of claim 1 wherein said extract is present in about 0.5 weight percent.

5. The composition of claim 2 wherein the innocuous carrier is a liquid.

* * * * *